United States Patent [19]

Kasina et al.

[11] Patent Number: 5,252,721
[45] Date of Patent: Oct. 12, 1993

[54] S₃N CHELATING COMPOUNDS

[75] Inventors: Sudhakar Kasina; Ananthachari Srinivasan, both of Kirkland, Wash.

[73] Assignee: NeoRx Corporation, Seattle, Wash.

[21] Appl. No.: 591,104

[22] Filed: Sep. 28, 1990

[51] Int. Cl.$^5$ ............................................. C07F 5/00
[52] U.S. Cl. ..................................... 534/14; 534/10
[58] Field of Search ................... 424/1.1; 534/10, 14; 530/391.3, 391.5

[56] References Cited

U.S. PATENT DOCUMENTS

| | | |
|---|---|---|
| 2,810,753 | 10/1957 | Bersworth . |
| 4,571,430 | 2/1986 | Byrne et al. . |
| 4,789,736 | 12/1988 | Canning et al. . |
| 4,839,467 | 6/1989 | Deutsch ............................ 424/1.1 |
| 4,849,511 | 7/1989 | Verbruggen . |
| 4,861,869 | 8/1989 | Nicolotti et al. . |
| 4,883,862 | 11/1989 | Chervu et al. . |
| 4,897,255 | 1/1990 | Fritzberg et al. . |
| 4,963,682 | 10/1990 | Bodor . |
| 4,963,688 | 10/1990 | Bodor . |
| 4,965,392 | 10/1990 | Fritzberg et al. . |
| 4,988,496 | 1/1991 | Srinivasan et al. . |

OTHER PUBLICATIONS

Lever et al., *Tetrahedron Letters*, vol. 29, No. 26, pp. 3219-3222, 1988 (printed in Great Britain), "Synthesis of a novel bifunctional chelate designed for labeling proteins with technetium-99m" Mastrostamatis et al., *Eur. J. Nucl. Med., Suppl. to vol. 16*, 1990.
Abstract No. 428, "Tripodal N,S₃-donor ligands as a new backbone for reduced technetium".
Corbin et al., *Inorganica Chimica Acta*, 90 (1984), pp. 41-51, "Preparation and properties of tripodal and linear tetradentate N,S-donor ligands and their complexes containing the MoO₂²⁺ core".

*Primary Examiner*—Robert L. Stoll
*Assistant Examiner*—Matthew Zmurko
*Attorney, Agent, or Firm*—Seed and Berry

[57] ABSTRACT

Novel chelating compounds and the corresponding radionuclide metal chelates are useful for radiolabeling proteins such as antibodies with radionuclide metals such as $^{99m}$Tc, $^{186}$Re, and $^{188}$Re. The chelating compounds are of the following formulas:

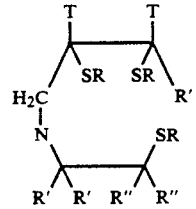

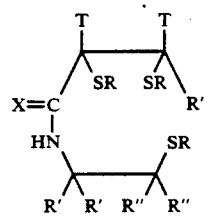

wherein
each R is a protecting group;
Q is hydrogen or a protecting group;
each T is independently chosen from hydrogen, lower alkyl groups of from 1 to about 6 carbon atoms, electron withdrawing groups, and lower alkyl groups of from 1 to about 6 carbon atoms substituted with electron withdrawing group(s);
X represents O, S, or NH;
each R' is independently selected from:
—(CH$_2$)$_n$—COOH with n=0 to about 4,
—(CH$_2$)$_n$—Z, wherein Z represents a conjugation group and n is 0 to about 4,
hydrogen, and
a lower alkyl group of from 1 to about 6 carbon atoms;
each R" is independently selected from:
—(CH$_2$)$_n$—COOH, with n=0 to about 4,
hydrogen, and
a lower alkyl group of from 1 to about 6 carbon atoms; and
the compound comprises at least one —(CH$_2$)$_n$—Z substituent.

The conjugation group Z reacts with a protein to bind the chelating compound thereto. The radiolabeled proteins have diagnostic or therapeutic use, depending on the radionuclide metal chosen.

8 Claims, No Drawings

S₃N CHELATING COMPOUNDS

BACKGROUND

Radiolabeled proteins such as antibodies are used in a variety of diagnostic and therapeutic medical procedures. The increased specificity of monoclonal antibodies, compared to polyclonal antibodies, makes them even more useful for delivering diagnostic or therapeutic agents such as radioisotopes to desired target sites in vivo. A monoclonal antibody specific for a desired type of target cells such as tumor cells may be used to deliver a therapeutic radionuclide attached to the antibody to the target cells, thereby causing the eradication of the undesired target cells. Alternatively a monoclonal antibody having a diagnostically effective radionuclide attached thereto may be administered, whereupon the radiolabeled antibody localizes on the target tissue. Conventional diagnostic procedures then may be used to detect the presence of the target sites within the patient.

One method for radiolabeling proteins such as antibodies involves attachment of radionuclide metal chelates to the proteins. Chelates having a variety of chemical structures have been developed for this purpose. The usefulness of such chelates is dependent upon a number of factors such as the stability of radionuclide binding within the chelate and the reactivity of the chelating compound with the desired protein. The efficiency of radiolabeling of the chelating compound to produce the desired radionuclide metal chelate also is important. Another consideration is the biodistribution of the radiolabeled protein and catabolites thereof in vivo. Localization in non-target tissues limits the total dosage of a therapeutic radiolabeled protein that can be administered, thereby decreasing the therapeutic effect. In diagnostic procedures, localization in non-target tissues may cause undesirable background and/or result in misdiagnosis. The need remains for improvement in these and other characteristics of radionuclide metal chelate compounds used for radiolabeling of proteins such as antibodies.

SUMMARY OF THE INVENTION

The present invention provides chelating compounds useful as protein labeling reagents, the corresponding radionuclide metal chelates, and targeting molecules such as proteins radiolabeled therewith. The radiolabeled proteins of the present invention have use in various assays as well as in vivo diagnostic and therapeutic procedures. The protein may be a monoclonal antibody that binds to cancer cells, for example.

The chelating compounds of the present invention include compounds of the formulas:

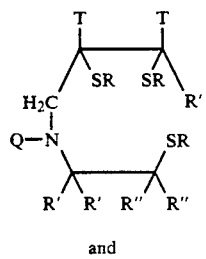
(I)

and

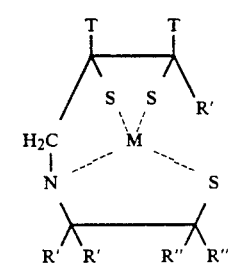
(II)

wherein:
each R is a protecting group;
Q is hydrogen or a protecting group;
each T is independently chosen from hydrogen, lower alkyl groups of from 1 to about 6 carbon atoms, electron withdrawing groups, and lower alkyl groups of from 1 to about 6 carbon atoms substituted with electron withdrawing group(s);
X represents O, S, or NH;
each R' is independently selected from:
  —(CH₂)$_n$—COOH with n=0 to about 4,
  —(CH₂)$_n$—Z, wherein Z represents a conjugation group and n=0 to about 4,
  hydrogen, and
  a lower alkyl group of from 1 to about 6 carbon atoms;
each R" is independently selected from:
  —(CH₂)$_n$—COOH, with n=0 to about 4,
  hydrogen, and
  a lower alkyl group of from 1 to about 6 carbon atoms; and
the compound comprises at least one —(CH₂)$_n$—Z substituent. The conjugation group Z serves to react with a protein to bind the chelating compound thereto.

The compounds of formulas I and II are reacted with molecules such as proteins to attach the compounds to the proteins. The compounds may be radiolabeled before or after attachment to the protein. The resulting radiolabeled proteins have diagnostic or therapeutic use, depending on the particular radionuclide employed.

The nitrogen atom and three sulfur atoms shown in formulas (I) and (II) are believed to function as donor atoms that are bonded to the radionuclide metal in the corresponding chelate. The compounds of formulas (I) and (II) thus may be designated S₃N chelating compounds.

Radiolabeling of the chelating compounds of formulas I and II produces the radionuclide metal chelates of formulas III and IV, respectively:

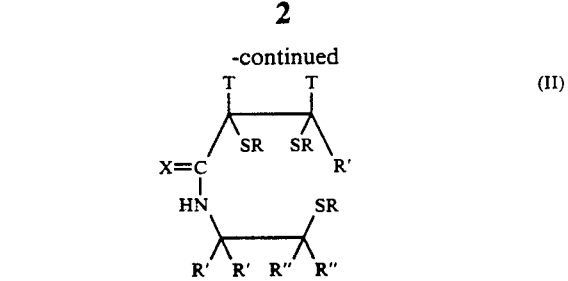
III

-continued

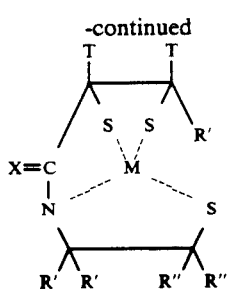
IV wherein M represents a radionuclide metal or oxide thereof and the other symbols are as defined above. Preferred radionuclide metals include $^{99m}$Tc, $^{188}$Re, and $^{186}$Re.

The present invention also provides protein-chelating compound conjugates resulting from reaction of a Z group of compounds I or II with a protein. Radiolabeled proteins comprising a radionuclide metal chelate of formula III or IV attached to a targeting protein also are provided by the present invention.

DETAILED DESCRIPTION OF THE INVENTION

The present invention provides chelating compounds useful as protein labeling reagents, methods for radiolabeling proteins using these reagents, and the resulting radiolabeled proteins having use in diagnostic or therapeutic procedures. The protein labeling reagents are of the following formulas I and II:

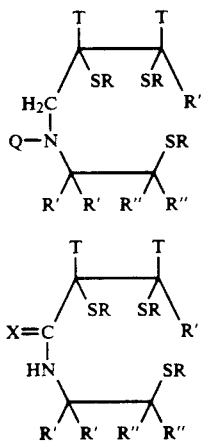

wherein:
each R is a protecting group;
Q is hydrogen or a protecting group;
each T is independently chosen from hydrogen, lower alkyl groups of from 1 to about 6 carbon atoms, electron withdrawing groups (e.g., nitro, sulfonate, or carboxylic acid groups), and lower alkyl groups of from 1 to about 6 carbon atoms substituted with electron withdrawing group(s);
X represents O, S, or NH;
each R' is independently selected from:
—(CH$_2$)$_n$—COOH with n=0 to about 4,
—(CH$_2$)$_n$—Z, wherein Z represents a conjugation group and n=0 to about 4,
hydrogen, and
a lower alkyl group of from 1 to about 6 carbon atoms (preferably 1 or 2 carbon atoms);
each R" is independently selected from:

—(CH$_2$)$_n$—COOH, with n=0 to about 4,
hydrogen, and
a lower alkyl group of from 1 to about 6 carbon atoms (preferably 1 or 2 carbon atoms); and
the compound comprises at least one —(CH$_2$)$_n$—Z substituent.

For the reagents of formulas (I) and (II), the two T substituents preferably are identical (preferably, both are methyl groups, most preferably, both are hydrogen).

Further, the compounds preferably comprise only one —(CH$_2$)$_n$—COOH substituent and only one —(CH$_2$)$_n$—Z substituent. The —(CH$_2$)$_n$—COOH substituent generally increases the water solubility of the compound.

The conjugation group Z is a functional group that will react with a functional group on a molecule to be radiolabeled (e.g., a targeting protein) thereby attaching the chelating compound thereto. Radiolabeling of the chelating compound produces a radionuclide metal chelate attached to the targeting protein. The chelating compounds of the present invention each comprise at least one conjugation group, as described in more detail below.

In the compound of formula I, Q represents hydrogen or any suitable nitrogen protecting group (a number of which are known) such as an alkyl group of 1 to 6 carbon atoms. Q preferably is hydrogen or a methyl group.

For the compounds of formula II, X preferably is O.

R represents any suitable sulfur protecting group. A number of protecting groups, including but not limited to acyl, aryl, and alkyl groups, are known for use in protecting sulfur atoms. The protecting groups should be removable, either prior to or during the radiolabeling reaction. The protecting groups on the three sulfur atoms may be the same or different. In some cases, a single protecting group (e.g., a thioacetal) may serve to protect two sulfur atoms, as shown below.

Among the suitable sulfur protecting groups are hemithioacetal, thioacetal, benzyl, and acetamidomethyl protecting groups. Also useful are acyl type groups such as those of the formula

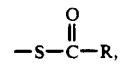

wherein the S is a sulfur atom of the chelating compound and R is an alkyl or aryl group. Examples are isobutyryl, benzoyl, and acetyl protecting groups.

When hemithioacetal protective groups are used, each sulfur atom to be protected has a separate protective group attached to it, which together with the sulfur atom defines a hemithioacetal group. The hemithioacetal groups contain a carbon atom bonded directly (i.e., without any intervening atoms) to a sulfur atom and an oxygen atom, i.e.,

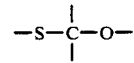

Preferred hemithioacetals generally are of the following formula, wherein the sulfur atom is a sulfur atom of the chelating compound:

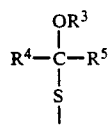

wherein R³ is a lower alkyl group, preferably of from two to five carbon atoms, and R⁴ is a lower alkyl group, preferably of from one to three carbon atoms. Alternatively, R³ and R⁴ may be taken together with the carbon atom and the oxygen atom shown in the formula to define a nonaromatic ring, preferably comprising from three to seven carbon atoms in addition to the carbon and oxygen atoms shown in the formula. R⁵ represents hydrogen or a lower alkyl group wherein the alkyl group preferably is of from one to three carbon atoms. Examples of such preferred hemithioacetals include, but are not limited to:

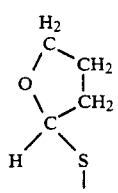

Tetrahydrofuranyl

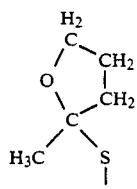

2-methyl tetrahydrofuranyl

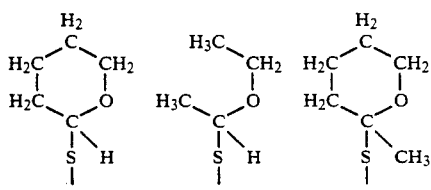

Tetrahydropyranyl  ethoxyethyl  2-methyl tetrahydropyranyl

Other hemithioacetal sulfur protecting groups include those derived from monosaccharides, such as the following, wherein the sulfur atom is a sulfur donor atom of the chelating compound:

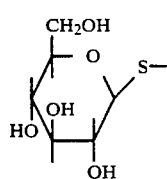

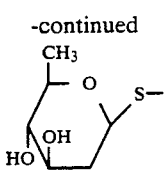

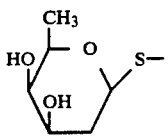

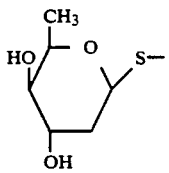

and

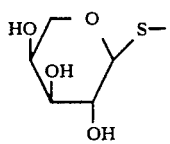

Examples of thioacetal protecting groups are as follows, wherein two sulfur atoms (the two sulfur atoms attached to adjacent carbon atoms in the chelating compound) are attached to a single protecting group:

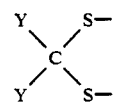

wherein each Y is independently selected from hydrogen, alkyl groups of 1 to 6 carbons (preferably methyl or ethyl), alkoxy groups of 1 to 6 carbons (preferably 1 or 2 carbon atoms), phenyl groups, and phenyl rings having an electron donating group (e.g., hydroxy, methoxy, or ethoxy group) bonded directly thereto. The two sulfur atoms shown are sulfur donor atoms of the chelating compound which, together with the protecting group, form the thioacetal group. Suitable thioacetals include, but are not limited to, the following:

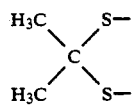

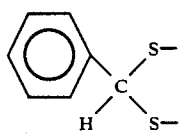

Representative examples of the compounds of formula (I) include, but are not limited to:

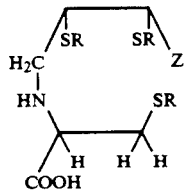

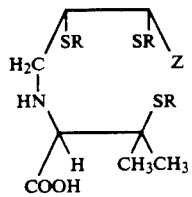

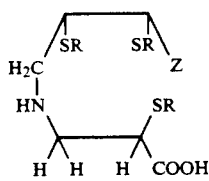

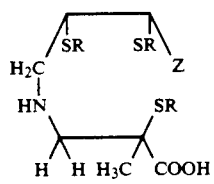

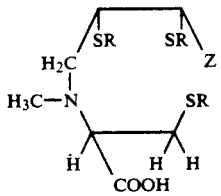

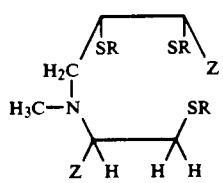

Representative examples of the compounds of formula (II) include but are not limited to:

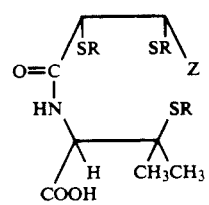

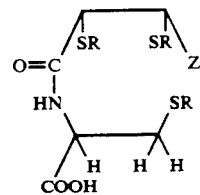

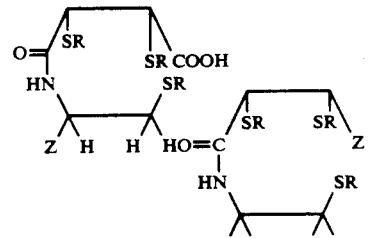

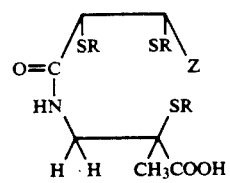

In preferred chelating compounds of the present invention, Z represents an active ester (described below). The two sulfur atoms that are attached to immediately adjacent carbon atoms (i.e., the vicinal dithiol portion of the compound) preferably are attached to a single protecting group (e.g., a thioacetal). The remaining sulfur atom preferably is protected by a different group such as a benzyl group.

The compounds of formulas I and II are useful as reagents for radiolabeling other molecules. The chelating compounds may be attached to the molecule to be radiolabeled either before or after the radiolabeling reaction. The molecule should contain (or be modified to contain) a functional group such as a primary amine or sulfhydryl that will react with the conjugation group on the chelating compound. The molecule may be any such molecule to be radiolabeled for use in in vitro assays, diagnostic or therapeutic procedures in vivo, or other such purpose.

In one embodiment of the invention, the molecule to be radiolabeled is a targeting molecule. The targeting molecule is any molecule that will serve to deliver the radionuclide metal chelate to a desired target site (e.g., target cells) in vitro or in vivo. Examples of targeting molecules include, but are not limited to, steroids, lymphokines, and those drugs and proteins that bind to a desired target site.

The targeting molecule may be a targeting protein, which is capable of binding to a desired target site. The term "protein" as used herein includes proteins, polypeptides, and fragments thereof. The targeting protein may bind to a receptor, substrate, antigenic determinant, or other binding site on a target cell or other target site. The targeting protein serves to deliver the radionuclide attached thereto to a desired target site in vivo. Examples of targeting proteins include, but are not limited to, antibodies and antibody fragments, hormones, fibrinolytic enzymes, and biologic response modifiers. In addition, other polymeric molecules that localize in a desired target site in vivo, although not strictly proteins, are included within the definition of the term "targeting proteins" as used herein. For example, certain carbohydrates or glycoproteins may be used in the present invention. The proteins may be modified, e.g., to produce variants and fragments thereof, as long as the desired biological property (i.e., the ability to localize at the target site) is retained. The proteins may be modified by using various genetic engineering or protein engineering techniques, for example.

Among the preferred targeting proteins are antibodies, most preferably monoclonal antibodies. A number of monoclonal antibodies that bind to a specific type of cell have been developed, including monoclonal antibodies specific for tumor-associated antigens in humans. Among the many such monoclonal antibodies that may be used are anti-TAC, or other interleukin-2 receptor antibodies; 9.2.27 and NR-ML-05, reactive with the 250 kilodalton human melanoma-associated proteoglycan; and NR-LU-10, reactive with a pancarcinoma glycoprotein. The antibody employed in the present invention may be an intact (whole) molecule, a fragment thereof, or a functional equivalent thereof. Examples of antibody fragments are F(ab')$_2$, Fab', Fab, and F, fragments, which may be produced by conventional methods or by genetic or protein engineering.

The chelating compounds of the present invention comprise at least one (and preferably only one) conjugation group Z. A conjugation group is a chemically reactive functional group that will react with a molecule to be radiolabeled to bind the chelating compound thereto. When the targeting molecule is a protein, the conjugation group is reactive under conditions that do not denature or otherwise adversely affect the protein. Examples of suitable conjugation groups include but are not limited to active esters, isothiocyanates, amines, hydrazines, maleimides or other Michael-type acceptors, thiols, and activated halides. Among the preferred active esters are N-hydroxysuccinimidyl ester, sulfosuccinimidyl ester, thiophenyl ester, 2,3,5,6-tetrafluorophenyl ester, and 2,3,5,6-tetrafluorothiophenyl ester. The latter three preferred active esters may comprise a group that enhances water solubility, at the para (i.e., 4) or the ortho position on the phenyl ring. Examples of such groups are $CO_2H$, $SO_3^-$, $PO_3^{2-}$, $OPO_3^{2-}$, $OSO_3^-$, $N^+R_3$ wherein each R represents H or an alkyl group, and $O(CH_2CH_2O)_nCH_3$ groups.

Proteins contain a variety of functional groups; e.g., carboxylic acid (COOH) or free amine (—NH$_2$) groups, which are available for reaction with a suitable conjugation group on a chelating compound to bind the chelating compound to the protein. For example, an active ester on the chelating compound reacts with epsilon amine groups on lysine residues of proteins to form amide bonds. Alternatively, a targeting molecule and/or a chelator may be derivatized to expose or attach additional reactive functional groups. The derivatization may involve attachment of any of a number of linker molecules such as those available from Pierce Chemical Company, Rockford, Ill. Alternatively, the derivatization may involve chemical treatment of the protein (which may be an antibody). Procedures for generation of free sulfhydryl groups on antibodies or antibody fragments by reducing disulfide bonds are also known. Maleimide conjugation groups on a chelating compound are reactive with the sulfhydryl (thiol) groups.

Alternatively, when the targeting molecule is a carbohydrate or glycoprotein, derivatization may involve chemical treatment of the carbohydrate; e.g., glycol cleavage of the sugar moiety of a glycoprotein antibody with periodate to generate free aldehyde groups. The free aldehyde groups on the antibody may be reacted with free amine or hydrazine conjugation groups on the chelator to bind the chelator thereto. (See U.S. Pat. No. 4,671,958.)

The chelating compounds of the present invention are radiolabeled, using conventional procedures, with any of a variety of radionuclide metals to form the corresponding radionuclide metal chelates. The radiolabeling may be conducted before or after the chelating compound is attached to the molecule to be radiolabeled. These radionuclide metals include, but are not limited to, copper (e.g., $^{67}Cu$ and $^{64}Cu$); technetium (e.g., $^{99m}Tc$); rhenium (e.g., $^{186}Re$ and $^{188}Re$); lead (e.g., $^{212}Pb$); bismuth (e.g., $^{212}Bi$); palladium (e.g., $^{109}Pd$); and rhodium (e.g., $^{105}Rh$). Methods for preparing these isotopes are known. Molybdenum/technetium generators for producing $^{99m}Tc$ are commercially available. Procedures for processing $^{186}Re$ include the procedures described by Deutsch et al., (*Nucl. Med. Biol.* Vol. 13:4:465-477, 1986) and Vanderheyden et al. (*Inorganic Chemistry*, Vol. 24:1666-1673, 1985), and methods for production of $^{188}Re$ have been described by Blachot et al. (*Int. J. Applied Radiation and Isotopes* Vol. 20:467-470, 1969) and by Klofutar et al. (*J. of Radioanalytical Chem.*, Vol. 5:3-10, 1970). Production of $^{109}Pd$ is described in Fawwaz et al., *J. Nucl. Med.* (1984), 25:796. Production of $^{212}Pb$ and $^{212}Bi$ is described in Gansow et al., *Amer. Chem. Soc. Symp. Ser.* (1984), 241:215-217, and Kozah et al., *Proc. Nat'l. Acad. Sci. USA* (January 1986) 83:474-478. $^{99m}Tc$ is preferred for diagnostic use, and the other radionuclides listed above have therapeutic use.

The radionuclide advantageously is in chelatable form when reacted with the chelating compounds of the invention. In the case of technetium and rhenium, being in "chelatable form" generally requires a reducing step. A reducing agent will be employed to reduce the radionuclides (e.g., in the form of pertechnetate and perrhenate, respectively) to a lower oxidation state at which chelation will occur. Many suitable reducing agents, and the use thereof, are known. (See, for example, U.S. Pat. Nos. 4,440,738; 4,434,151; and 4,652,440.) Such reducing agents include, but are not limited to, stannous ion (e.g., in the form of stannous salts such as stannous chloride or stannous fluoride), metallic tin, ferrous ion (e.g., in the form of ferrous salts such as ferrous chloride, ferrous sulfate, or ferrous ascorbate) and many others. Sodium pertechnetate (i.e., $^{99m}TcO_4-$ which is in the +7 oxidation level) or sodium perrhenate (i.e., $^{188}ReO_4-$, $^{186}ReO_4-$) may be combined simultaneously with a reducing agent and a chelating compound of the invention in accordance with the radiolabeling method of the invention, to form a chelate.

Preferably, the radionuclide is treated with a reducing agent and a complexing agent to form an intermediate complex (i.e., an "exchange complex"). Complexing agents are compounds which bind the radionuclide more weakly than do the chelate compounds of the invention, and may be weak chelators. Any of the suitable known complexing agents may be used, including but not limited to gluconic acid, glucoheptonic acid, methylene disphosphonate, glyceric acid, glycolic acid, tartaric acid, mannitol, oxalic acid, malonic acid, succinic acid, bicine, malic acid, N,N'-bis(2-hydroxy ethyl) ethylene diamine, citric acid, ascorbic acid and gentisic acid. Good results are obtained using gluconic acid or glucoheptonic acid as the technetium-complexing agent and citric acid for rhenium. When the radionuclide in the form of such an exchange complex is reacted with the chelating compounds of the invention (which may be attached to a targeting protein), the radionuclide will transfer to these chelating compounds which bind the radionuclide more strongly to form chelates of the invention. Radionuclides in the form of such exchange complexes also are considered to be in "chelatable form" for the purposes of the present invention.

Chelates of $^{212}Pb$, $^{212}Bi$, $^{103}Rh$, and $^{109}Pd$ may be prepared by combining the appropriate salt of the radionuclide with the chelating compound and incubating the reaction mixture at room temperature or at higher temperatures. It is not necessary to treat the lead, bismuth, rhodium, palladium, and copper radioisotopes with a reducing agent prior to chelation, as such isotopes are already in an oxidation state suitable for chelation (i.e., in chelatable form).

The specific radiolabeling reaction conditions may vary somewhat according to the particular radionuclide and chelating compound involved. When the chelating compound is attached to a targeting protein prior to radiolabeling, the radiolabeling reaction is conducted under physiologically acceptable conditions to avoid denaturing or otherwise damaging the protein.

The present invention also provides a method for radiolabeling targeting proteins by attaching a chelating compound of formula I or II to the protein, then reacting the resulting protein-chelating compound conjugate with a radionuclide metal in chelatable form. Alternatively, the chelating compound is first reacted with a radionuclide metal in chelatable form, and the resulting radionuclide metal chelate is reacted with the protein. In either case, a protein having a radionuclide metal chelate attached thereto is produced. Details of these reactions are presented in the examples below.

The invention thus provides protein-chelating compound conjugates of formulas V and VI, produced by reacting a protein with a chelating compound of formula I or II, respectively:

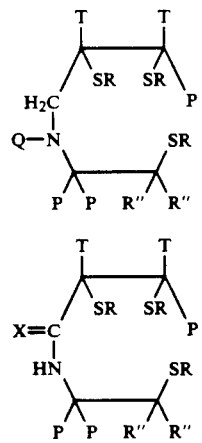

wherein:
one P represents a substituent —$(CH_2)_n$—P' with n=0 to about 4 and P' representing a protein; and the remaining substituents P are independently selected from:

—$(CH_2)_n$—COOH with n=0 to 4,
hydrogen, and
a lower alkyl group of from 1 to about 6 carbon atoms;

with the other symbols having the definition presented for formulas I and II above.

Also provided by the present invention are radiolabeled proteins of the following formulas:

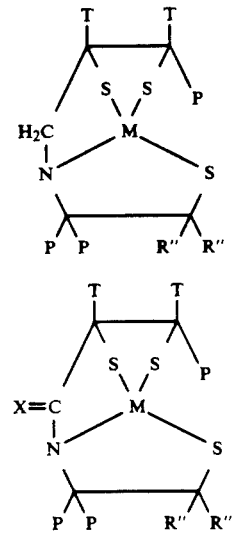

wherein:
M represents a radionuclide metal or oxide thereof;
one P represents a substituent —$(CH_2)_n$—P' with n=0 to about 4 and P' representing a protein; and the remaining substituents P are independently selected from:

—$(CH_2)_n$—COOH with n=0 to about 4,
hydrogen, and
a lower alkyl group of from 1 to about 6 carbon atoms;

with the other symbols having the definition presented for formulas I and II above.

The protein P' may be a targeting protein as described above. It is to be understood that the protein P' may include a portion of the conjugation group Z that reacted with the protein.

The radiolabeled targeting proteins of the present invention have use in diagnostic and therapeutic procedures, both for in vitro assays and for in vivo medical procedures. The radiolabeled molecules may be administered intravenously, intraperitoneally, intralymphatically, locally, or by other suitable means, depending on such factors as the type of target site. The amount to be administered will vary according to such factors as the type of radionuclide (e.g., whether it is a diagnostic or therapeutic radionuclide), the route of administration, the type of target site(s), the affinity of the targeting protein for the target site of interest, and any cross-reactivity of the targeting protein with normal tissues. Appropriate dosages may be established by conventional procedures and a physician skilled in the field to which this invention pertains will be able to determine a suitable dosage for a patient. A diagnostically effective dose is generally from about 5 to about 35 and typically from about 10 to about 30 mCi per 70 kg body weight. A therapeutically effective dose is generally from about 20 mCi to about 300 mCi. For diagnosis, conventional non-invasive procedures (e.g., gamma cameras) are used to detect the biodistribution of the diagnostic radionuclide, thereby determining the presence or absence of the target sites of interest (e.g., tumors).

The following examples are presented to illustrate certain embodiments of the invention, and are not to be construed as limiting the scope of the present invention.

EXAMPLE I

Synthesis of a Chelating Compound

The synthesis procedure is generally depicted in the following reaction scheme:

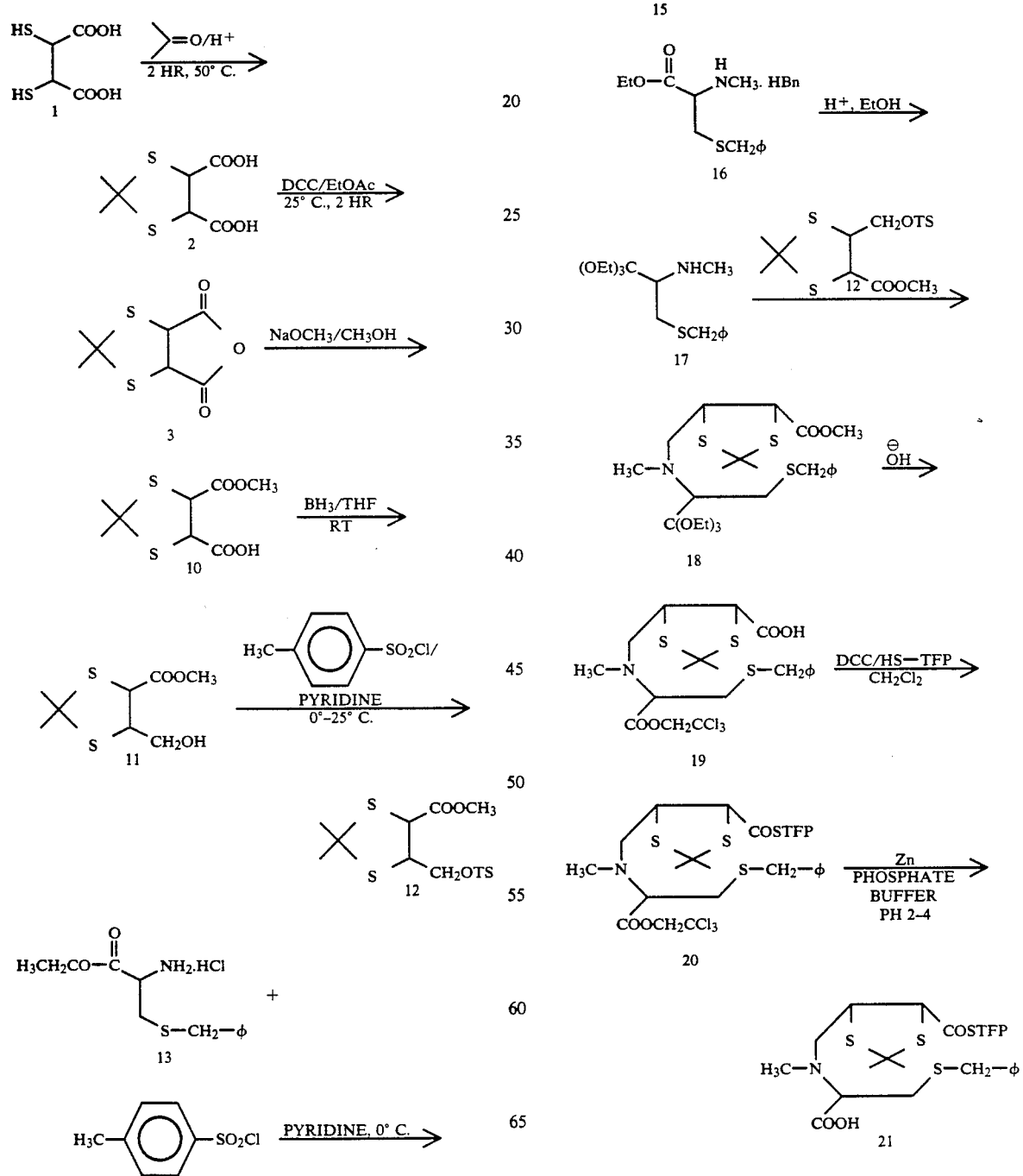

S,S'-Isopropylidene 2,3-dimercaptosuccinic acid (2)

To 1.0 g of meso 2,3-dimercaptosuccinic acid (DMSA), 50 mL of anhydrous acetone followed by 0.3 mL (6 drops) perchloric acid were added. The heterogeneous suspension was heated at 50° C. for 2 hours. Solvent from the clear light golden yellow solution was removed under reduced pressure. To the dried residue 50 mL water was added and extracted with ethyl acetate three times, each time with 100 mL. The combined ethyl acetate extracts were dried over anhydrous sodium sulfate and the solvent was removed in vacuo. The dry solid was dissolved in ether and the compound was precipitated by the addition of petroleum ether. The solid was filtered to give 0.9 g (74%) of 2 as a white compound which was recrystallized from $CHCl_3$/hexane to give crystals, MP 158°–160° C. $^1H$ NMR ($d_6$ acetone) $\delta$ 4.85 (S,2H), $\delta$ 1.8, 1.9 (2S,6H).

S,S'-Isopropylidene 2,3-dimercaptosuccinic anhydride (3)

To 0.8 g (3.6 mmol) of S,S'-isopropylidene 2,3-dimercaptosuccinic acid (2), 10 mL of ethyl acetate was added. To this solution with stirring was added a solution of 1,3-dicyclohexylcarbodiimide 0.82 g (0.396 mmol) in 10 mL ethyl acetate. After stirring the reaction mixture at room temperature for two hours, the reaction mixture was filtered to remove the dicyclohexyl urea, a byproduct of the reaction. Removal of the solvent from the filtrate left a white solid. The crude product was purified by sublimation to give 0.52 g (71%) of S,S'-isopropylidene 2,3-dimercaptosuccinic anhydride (3), mp 141°–142° C. $^1H$ NMR ($d_6$ acetone) $\delta$ 5.5 (S,2H), $\delta$ 1.8 (S,6H).

3-Carbomethoxy S,S'-isopropylidene 2,3-dimercaptopropionic acid (10)

Prepare a fresh 0.011 mol sodium methoxide in methanol solution by dissolving 0.26 g of sodium in 50 mL of anhydrous methanol. Then 1.0 g of S,S'-isopropylidene 2,3-dimercaptosuccinic anhydride is added to the reaction mixture and stirred at room temperature. Completion of the reaction is followed by thin layer chromatography. Add 25 mL of prewashed (water followed by methanol) BIORAD AG 50W-X4 (H+) cation exchange resin and stir for 15 minutes. Then filter off the resin and wash it thoroughly with 25 mL methanol. Concentrate the filtrate to a residue on a rotatory evaporator. Add 15 mL heptane and evaporate the solvent to a dry residue to yield grey solid.

3-Carbomethoxy S,S'-isopropylidene 2,3-dimercaptopropanol (11)

To a solution of S,S'-isopropylidene 3-carbomethoxy 2,3-dimercaptopropionic acid in tetrahydrofuran at 35°–40° C. is rapidly added $BH_3$-THF (0.18 mmol). After three hours, an aliquot is analyzed by thin layer chromatography (ethyl acetate:hexane=4:1). Disappearance of the starting material is an indication of complete conversion to the alcohol. 10 mL of ethanol is added to the reaction mixture and the mixture is evaporated to dryness. After repeating the procedure twice with 20 mL of ethanol, the residue is suspended in water, extracted with ethyl acetate and the organic layer is washed successively with 2×15 mL of 2% aqueous bicarbonate and water followed by drying over anhydrous sodium sulfate. The organic solvent is then evaporated, the residue dissolved in hexane and upon cooling gives S,S'-isopropylidene 3-carbomethoxy 2,3-dimercaptopropanol (11) in high yield.

3-Carbomethoxy S,S'-isopropylidene 2,3-dimercaptopropanol tosylate (12)

The alcohol S,S'-isopropylidene 3-carbomethoxy 2,3-dimercaptopropanol (11, 1.0 g, 4.5 mmol) prepared above is dissolved in 5 mL of pyridine (0° C.–5° C.) and 0.9 g (4.7 mmol) of p-toluenesulfonyl chloride added at once. Precipitation of pyridinium hydrochloride is observed after one hour and the mixture is stirred for additional two hours, followed by storage at 4° C. overnight. The solution is poured with stirring into 50 mL of ice water and the resulting solid is isolated by filtration, washed with water and dried under vacuum in a desicator overnight to yield 60–80% of the tosyl ester, S,S'-isopropylidene 3-carbomethoxy 2,3-dimercaptopropanol tosyl ester, 12.

N-Tosyl-S-benzylcysteine ethyl ester (14)

S-benzylcysteine ethyl ester hydrochloride, 13 (5.0 g, 18.1 mmol) is dissolved in 25 ml of pyridine (0° C.–5° C.) and 3.5 g (18.3 mmol) of tosyl chloride is added at once. Precipitation of pyridinium hydrochloride is observed after one hour and the reaction mixture is stirred for an additional two hours, followed by storage at 4° C. overnight. The solution is poured with stirring into 150 mL of ice water and the resulting solid isolated by filtration, washed with ice cold water and dried under vacuum in a desicator overnight to yield 75–90% yield of S-benzyl cysteine ethyl ester tosylamide, 14. The crude product is recrystallized from ethyl acetate.

N-Tosyl-N-methyl S-benzylcysteine ethyl ester (15)

S-benzylcysteine ethyl ester tosylamide, 14 (5.0 g, 12.7 mmol) is dissolved in dimethylformamide. Solid sodium hydride (0.31 g, 12.9 mmol) is added. Then methyl iodide (1.9 g, 13.4 mmol) is added and the reaction mixture stirred at room temperature. Completion of the reaction is monitored by thin layer chromatography. Solvent from the reaction mixture is removed under vacuum and dried. The crude product is purified by flash chromatography to yield 50–75%- of S-benzylcysteine ethyl ester N-methyltosylamide, 15.

S-Benzyl N-methylcysteine ethyl ester hydrobromide (16)

Glacial acetic acid is saturated with hydrogen bromide gas. To the stirred HBr solution one equivalent of solid S-benzylcysteine ethyl ester N-methyltosylamide is added. The reaction mixture is stirred at room temperature for 2 to 4 hours. Solvent from the reaction mixture is removed under reduced pressure and dried under vacuum to yield 75–80% of S-benzyl N-Methylcysteine ethyl ester hydrobromide salt 16.

S-Benzyl N-methylcysteine triethyl orthoester (17)

S-benzyl N-methylcysteine ethyl ester hydrobromide is converted to its triethyl orthoesther using acid catalyst by conventional method. Completion of the reaction is monitored by thin layer chromatography. The crude product is purified by flash chromatography.

N-Methyl-N-($\beta$-benzylthio-$\alpha$-triethoxymethyl)ethyl-S,S'-isopropylidene-2,3-dimercapto-4-aminobutyric acid methyl ester (18)

S-benzyl N-methylcysteine triethylorthoester, 17 (3.0 g, 9.2 mmol) is dissolved in DMF. To the stirred solution at room temperature triethylamine (1.3 mL, 9.2 mmol) is added. Then, 3-carbomethoxy S,S'-isopropylidene 2,3-dimercaptopropanol tosylate, 12 (3.2 g, 9.2 mmol) is added and the reaction mixture is stirred at room temperature. The progress and completion of the reaction is followed by thin layer chromatography. Solvent from the reaction mixture is removed under vacuum and the resulting solid dried. The crude compound is purified by flash chromatography, to yield compound 18 in 60–80% yield.

N-Methyl-N-(β-benzylthio-α-trichloroethoxycarbonyl)ethyl-S,S'-isopropylidene-2,3-dimercapto-4-aminobutyric acid (19) Compound 18 is hydrolyzed conventionally with 1 equivalent of sodium hydroxide to N-Methyl-N-(β-benzylthio-α-trichloroethoxycarbonyl)ethyl-S,S'-isopropylidene-2,3-dimercapto-4-aminobutyric acid, 19. The crude product is purified by flash chromatography.

N-Methyl-N-(β-benzylthio-α-trichloroethoxycarbonyl)ethyl-S,S'-isopropylidene-2,3-dimercapto-4-aminobutyric acid-2',3',5',6'-tetrafluorothiophenyl ester (20)

To a solution of compound 19 (1.0 g, 18.3 mmol) and 2,3,5,6-tetrafluorothiophenol (0.35 g, 21.08 mmol) in 25 mL dichloromethane is added 1,3-dicyclohexylcarbodiimide (0.45 g, 21.9 mmol) with rapid stirring. The mixture is stirred at room temperature for 18 to 24 hours, or until TLC analysis indicates complete conversion to the tetrafluorothiophenyl ester. Then the mixture is cooled to 0° C., a few drops of acetic acid is added, and the mixture is stirred for a few minutes and then filtered. The filtrate is concentrated under vacuum to give a solid. The solid is dissolved in minimum amount of methylene chloride and allowed to stand at 5° C. for two to three hours. The solution is then filtered to remove any precipitated dicyclohexyl urea, and the filtrate is concentrated to afford solid compound 20. The solid is then washed with ether to remove any remaining 2,3,5,6-tetrafluorothiophenol. The crude compound is purified by flash chromatography on silica gel column.

N-Methyl-N-(β-benzylthio-α-carboxy)ethyl-S,S'-isopropylidene-2,3-dimercapto-4-aminobutyric acid-2',3',5',6'-tetrafluoro-thiophenyl ester (21)

To a solution of N-Methyl-N-(β-benzylthio-α-trichloroethoxycarbonyl)ethyl-S,S'-isopropylidene-2,3-dimercapto-4-aminobutyric acid-2,3',5',6'-tetrafluoro-thiophenyl ester 20 (0.5 g, 6.9 mmol) in 75 mL tetrahydrofuran, 1.4 mL of 1.0M $KH_2PO_4$ is added. To this solution, zinc dust (0.6 g, 91.9 mmol) is added. After stirring the reaction mixture at room temperature for 45 minutes, additional buffer (1.4 mL) and zinc dust (0.6 g) are added. The reaction mixture is sonicated for another hour. The TLC of the reaction mixture is an indication of completion of product formation. The mixture is sonicated for an additional hour. The reaction mixture is filtered, rinsed with acetonitrile, 50% $CH_3CN/H_2O$ with 1% acetic acid successively. The solvent is removed under reduced pressure. The residue is chromatographed on silica gel with 10% >—OH/$CH_2Cl_2$—2% HOAC and then 25% >—OH/$CH_2Cl_2$—2% HOAC as elution solvents.

Compound 21 is a chelating compound of the present invention, also referred to as a ligand elsewhere herein. "COSTFP" represents a 2,3,5,6-tetrafluorothiophenyl ester, which is a conjugation group.

EXAMPLE II

Synthesis of a Chelating Compound

A chelating compound of the present invention was synthesized as generally depicted in the following reaction scheme:

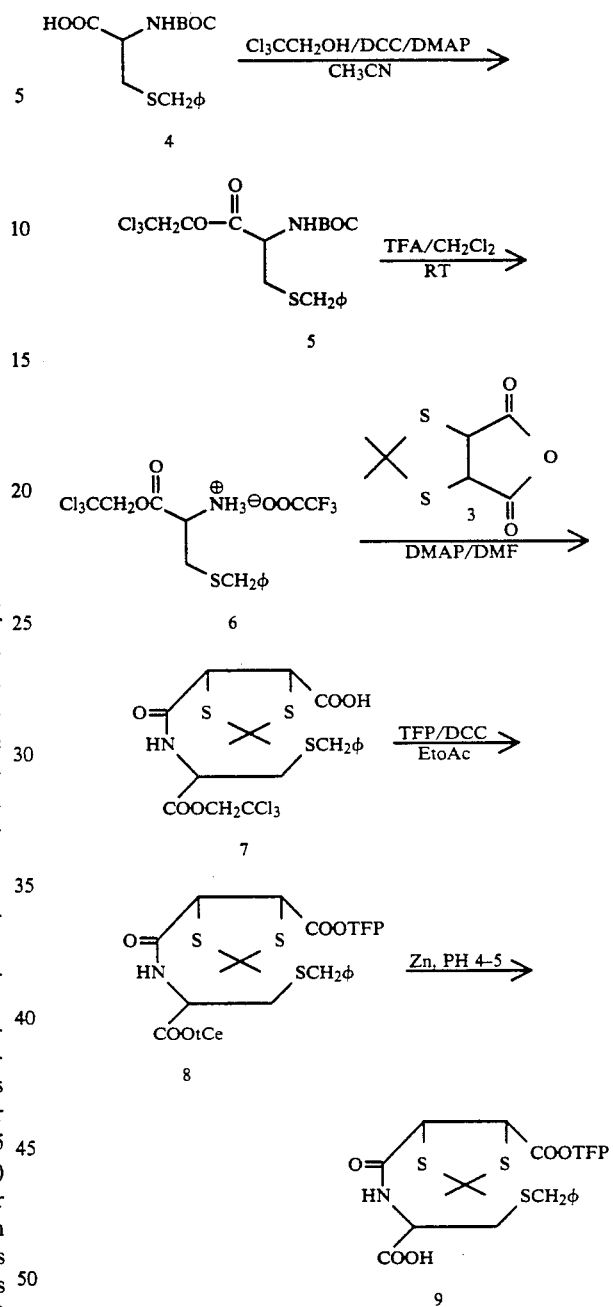

N-t-Butyloxycarbonyl S-benzyl L-cysteine trichloroethyl ester (5)

To an ice cold suspension of N-t-Butyloxycarbonyl S-benzyl cysteine 4 (5.0 g, 16.06 mmol) in 100 mL acetonitrile was added 4-dimethylaminopyridine (2.4 g, 19.6 mmol). To the solution was then added trichloroethanol (2.0 mL, 20.8 mmol). 1,3-dicyclohexylcarbodiimide (4.0 g, 19.4 mmol) was added as a solid. The ice bath was allowed to melt and the reaction mixture was stirred at room temperature for 15-18 hours. Analysis by thin layer chromatography indicated the reaction was complete. A few drops (8-10) of glacial acetic acid were added. The reaction mixture was cooled to 0° C. and the precipitate was filtered. The solvent from filtrate was removed in vacuo. The residue was dissolved in methylene chloride and washed with saturated sodium bicarbonate, brine, and water, respectively. Methylene chloride layer was dried over anhydrous sodium sulfate. After filtration and removal of solvent, a semi-solid was obtained which was purified by flash chromatography on a silica gel column using methylene chloride as an elution solvent to give 3.0 g of 5: $^1$H NMR (d$_6$-DMSO) 1.39 (S,9H), 2.6–2.9 (m,2H), 3.75 (S,2H), 4.15–4.35 (M,1H), 4.75–5.0 (Q,2H), 7.25 (S,5H), 7.40–7.55 (d, 1H).

S-Benzylcysteine 1,1,1-trichloroethylester trifluoroacetate (6)

1,1,1-trichloroethyl N-t-Butyloxycarbonyl S-benzyl cysteinate (1.5 g, 3.0 mmol) was dissolved in 10 mL methylene chloride. To the clear solution, 10 mL of trifluoroacetic acid was added and the reaction mixture was stirred at room temperature for one hour. Completion of the reaction was also monitored by thin layer chromatography on silica gel plates using methylene chloride as developing solvent. The solvent was removed under reduced pressure. The solid residue was washed twice with heptane and the solvent was removed under vacuum to give 1.5 g. The residue was dried under vacuum and used for further reactions without purification.

N-(3-Carboxy-S,S'-isopropylidene-2,3-dimercapto)-propionyl-S-benzylcysteine trichloroethyl ester (7)

To a solution of trichloroethyl S-benzylcysteine trifluoroacetate (1.54 g, 3.4 mmol) in 10 mL anhydrous dimethylformamide was added a solution of isopropylidene 2,3dimercaptosuccinic anhydride (0.75 g, 3.7 mmol) in 10 mL of dimethylformamide. To the reaction mixture was then added dimethylaminopyridine (1.0 g, 8.2 mmol) as a dry solid. The reaction mixture was stirred at room temperature overnight. The DMF from the reaction mixture was removed at low heat under vacuum. The semi-solid residue was dried and purified by flash chromatography on a silica gel column using ethyl acetate and ethyl acetate:acetic acid (98:2) as elution solvents successively.

N-(3-(2',3',5',6'-tetrafluorophenoxycarbonyl)-S,S'-isopropylidene-2,3-dimercapto)propionyl-S-benzylcysteine trichloroethyl ester (8)

To a solution of compound 7 (0.5 g, 0.0009 mol) and 2,3,5,6-tetrafluorophenol (0.3 g, 0.0018 mol) in 15 mL dichloromethane is added 1,3-dicyclohexyl carbodiimide (0.3 g, 0.0015 mol) with rapid stirring. The mixture is stirred at room temperature for 2 to 4 hours or until TLC analysis indicated complete conversion to the tetrafluorophenyl ester. Then the mixture is cooled to 0° C., a few drops of acetic acid are added, the mixture stirred for a few minutes, and then is filtered. The filtrate is concentrated under vacuum to give solid. The solid is dissolved in minimum amount of methylene chloride and allowed to stand at 5° C. for two to three hours. The solution is then filtered to remove any precipitated dicyclohexyl urea, and the filtrate is concentrated to afford solid N-(3-(2',3',5',6'-tetrafluorophenoxycarbonyl-S,S'-isopropylidene-2,3-dimercapto)propionyl-S-benzylcysteine trichloroethyl ester. The solid is then either washed with ether to remove any remaining 2,3,5,6-tetrafluorophenol or purified by flash chromatography on silica gel using CH$_2$Cl$_2$:IPA:-HOAC=90:5:5 as elution solvent. The solvent from eluent is removed under vacuum and dried.

N-(3-(2',3',5',6'-tetrafluorophenoxycarbonyl)-S,S'-isopropylidene-2,3-dimercapto)propionyl-S-benzylcysteine (9)

To a solution of compound 8 (0.21 g, 0.0003 mol) in 75 mL tetrahydrofuran, 0.56 mL of 1.0M KH$_2$PO$_4$ is added. To this solution, zinc dust (0.275 g, 0.004 mol) is added. After stirring the reaction mixture at room temperature for 45 minutes, additional buffer (0.56 mL) and zinc dust (0.275 g) are added. The reaction mixture is sonicated for another hour. The TLC of the reaction mixture is an indication of completion of product formation. The mixture is sonicated for an additional hour. The reaction mixture is filtered, then rinsed with acetonitrile, 50% CH$_3$CN/H$_2$O with 1% acetic acid successively. The solvent is removed under reduced pressure. The residue is chromatographed on silica gel with 10% >—OH/CH$_2$Cl$_2$—2% HOAC and then 25% >—OH/CH$_2$Cl$_2$—2% HOAC as elution solvents.

Compound 9 is a chelating compound of the present invention, also referred to as a ligand elsewhere herein. "COOTFP" represents a 2,3,5,6-tetrafluorophenyl ester, which is a conjugation group. It is to be noted that the thioacetal portion of the chelating compound may also be shown as:

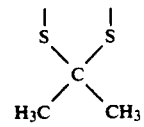

(the two different representations being equivalent).

EXAMPLE III

Conjugation of 2,3,5,6-Tetrafluorophenyl S-benzyl Cysteino 2,3-Dimercaptosuccinamidate to an Antibody The antibody used for derivatization is a monoclonal antibody fragment designated NR-LU-10 Fab, a murine antibody specific for human carcinoma surface antigen. The antibody is functionalized by dissolving the ligand, 2,3,5,6-tetrafluorophenyl S-benzyl cysteino 2,3-dimercaptosuccinamidate (compound 9 prepared in example II), in dimethylformamide solvent during derivatization with 70:1 molar offering of ligand to antibody. 100 μL of 20 mg/mL NR-LU-10 Fab in phosphate buffered saline is mixed with 300 μL of 0.2M phosphate buffer, pH 9.5. To the buffered antibody solution, 30 μL of 2.0 mg/mL ligand solution in DMF is added. The reaction mixture is incubated at room temperature for one hour. The resulting antibody-ligand conjugate is purified by size exclusion chromatography using a sephadex G-25 (PD-10) reversed phase column equilibrated with 0.2M sodium acetate buffer, pH 5.0. The 2.4–4.8 mL fractions off the PD-10 column are collected and used for radiolabeling with $^{99m}$Tc.

The antibody-ligand (i.e., chelating compound) conjugate is believed to be of the following chemical structure:

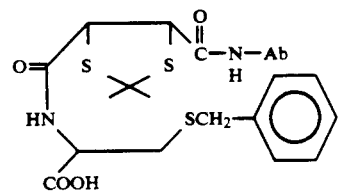

wherein Ab represents the antibody fragment and

is the amide bond formed by reaction of a primary amine on a lysine residue of the antibody with the active ester conjugation group on the chelating compound.

Chelating compound 21, produced in Example I, may be substituted for compound 9 in the procedures above to produce an antibody-ligand conjugate of the formula:

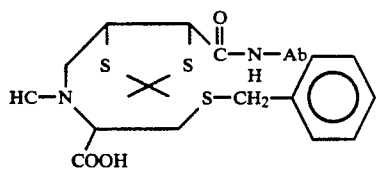

EXAMPLE IV

Preparation of Radiolabeled Proteins Tc-99m
Radiolabeling of Antibody-ligand Conjugate To 100 μL of a solution containing 5 mg of sodium gluconate and 0.1 mg of stannous chloride in water, 1.0 mL of $^{99m}TcO_4^-$ (pertechnetate) is added. After incubation at room temperature for one minute to form a $^{99m}$Tc-gluconate intermediate exchange complex, 200 μL of the $^{99m}$Tc-gluconate solution is mixed with 525 μL of freshly prepared PD-10 purified antibody-ligand conjugate (0.44 mg antibody-ligand conjugate prepared in example III). The reaction mixture is incubated at 37° C. for 15 minutes. The percentage of the Tc-99m from Tc-gluconate bound to the antibody-ligand conjugate is determined by standard instant thin layer chromatography (ITLC) in 12% trichloroacetic acid as a developing solvent. The native antibody fragment underivatized with ligand is used as a control. Minimal Tc-99m uptake in the control experiment is an indication that the Tc-99m uptake by the antibody-ligand conjugate is specific for the ligand and that non-specific Tc-99m uptake is negligible.

$^{188}$Re Chelates

The same chelating compound may be radiolabeled with $^{188}$Re by a procedure similar to the $^{99m}$Tc labeling procedure. Sodium perrhenate produced from a W-188/Re-188 research scale generator is combined with citric acid (a preferred complexing agent for $^{188}$Re), a reducing agent, and preferably gentisic acid and lactose. The resulting $^{188}$Re-citrate exchange complex is reacted with the desired chelating compound-antibody conjugate, as above. A Sephadex G-25 column may be used to purify the radiolabeled antibody. A $^{186}$Re-citrate exchange complex may be substituted in the same procedure.

The resulting radiolabeled antibodies (produced using antibody conjugates of ligands 9 and 21, respectively) are believed to have the following structures:

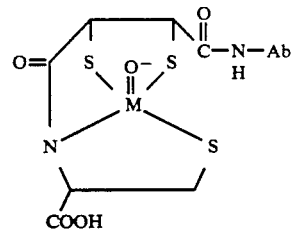

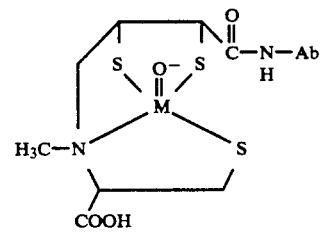

wherein M represents a radionuclide metal selected from $^{99m}$Tc, $^{188}$Re, and $^{186}$Re. Ab represents the antibody fragment, and

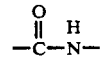

is the amide bond formed by the reaction of the primary amine on a lysine residue of the antibody with the active ester conjugation group on the chelating compound.

Other chelating compounds of formulas I and II may be attached to an antibody fragment and radiolabeled using the same procedures described above for chelating compounds 9 and 21. Other targeting proteins may be substituted for the antibody fragment in these procedures.

What is claimed is:

1. A radionuclide metal chelate of the formula:

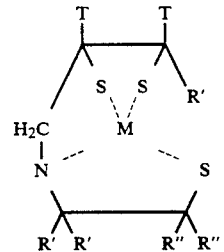

wherein:
M represents a radionuclide metal or oxide thereof selected from the group consisting of Cu, Tc, Re, Pb, Bi, Pd, and Rh;
each T is independently selected from the group consisting of hydrogen, lower alkyl groups of from 1 to about 6 carbon atoms, electron withdrawing groups, and lower alkyl groups of from 1 to about 6 carbon atoms substituted with electron withdrawing group(s);
each R' is independently selected from the group consisting of:
—(CH$_2$)$_n$—COOH with n=0 to about 4,
—(CH$_2$)$_n$—Z, wherein Z represents a conjugation group and n is 0 to about 4,
hydrogen, and a lower alkyl group of from 1 to about 6 carbon atoms;

each R" is independently selected from the group consisting of:
—$(CH_2)_n$—COOH, with n=0 to about 4,
hydrogen, and
a lower alkyl group of from 1 to about 6 carbon atoms; and the compound comprises at least one —$(CH_2)_n$—Z substituent.

2. A radionuclide metal chelate of the formula:

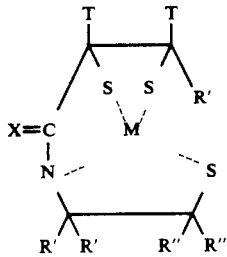

wherein:
M represents a radionuclide metal or oxide thereof selected from the group consisting of Cu, Tc, Re, Pb, Bi, Pd, and Rh;

each T is independently selected from the group consisting of hydrogen, lower alkyl groups of from 1 to 6 carbon atoms, electron withdrawing groups, and lower alkyl groups of from 1 to about 6 carbon atoms substituted with electron withdrawing group(s);

X represents O, S, or NH;

each R' is independently selected from the group consisting of:
—$(CH_2)_n$—COOH with n=0 to about 4,
—$(CH_2)_n$—Z, wherein Z represents a conjugation group and n is 0 to about 4,
hydrogen, and
a lower alkyl group of from 1 to about 6 carbon atoms;

each R" is independently selected from the group consisting of:
—$(CH_2)_n$—COOH, with n=0 to about 4,
hydrogen, and
a lower alkyl group of from 1 to about 6 carbon atoms; and the compound comprises at least one —$(CH_2)_n$—Z substituent.

3. The chelate of claim 2, wherein X is O.

4. The chelate of claim 1 or 2 wherein the radionuclide metal is selected from the group consisting of $^{99m}Tc$, $^{188}Re$, and $^{186}Re$.

5. The chelate of claim 1 or 2 wherein Z represents a conjugation group selected from the group consisting of active esters, isothiocyanates, amines, hydrazines, thiols, maleimides, and activated halides.

6. The chelate of claim 5 wherein the conjugation group is an active ester.

7. The chelate of claim 1 or 2 wherein one R' or R" substituent is —$(CH_2)_n$—COOH.

8. The chelate of claim 1 or 2 wherein T is hydrogen.

* * * * *